United States Patent
Yannacone, Jr. et al.

(10) Patent No.: US 8,233,968 B1
(45) Date of Patent: Jul. 31, 2012

(54) METHOD AND APPARATUS FOR HIGH RESOLUTION DYNAMIC DIGITAL INFRARED IMAGING

(75) Inventors: Victor John Yannacone, Jr., Patchogue, NY (US); Carol A. Yannacone, Patchogue, NY (US); Benjamin A. Rousseau, Somerville, MA (US); Jacob Green, Jacksonville, FL (US); William B. Hobbins, Madison, WI (US)

(73) Assignee: Victor John Yannacone, Jr., Patchogue, NY (US)

( * ) Notice: Subject to any disclaimer, the term of this patent is extended or adjusted under 35 U.S.C. 154(b) by 1669 days.

(21) Appl. No.: 10/019,904

(22) PCT Filed: Jun. 20, 2000

(86) PCT No.: PCT/US00/16851
§ 371 (c)(1),
(2), (4) Date: May 6, 2002

(87) PCT Pub. No.: WO00/78211
PCT Pub. Date: Dec. 28, 2000

(51) Int. Cl.
*A61B 6/00* (2006.01)
(52) U.S. Cl. ........ 600/473; 600/474; 600/310; 600/425; 600/407; 250/338.1; 250/339.01; 250/339.11; 250/339.14
(58) Field of Classification Search .................. 600/407, 600/425, 310, 473–477; 250/338.1, 339.01, 250/339.11, 339.14, 341.8
See application file for complete search history.

(56) References Cited

U.S. PATENT DOCUMENTS

| | | | | |
|---|---|---|---|---|
| 4,428,382 A | * | 1/1984 | Walsall et al. | 600/549 |
| 5,533,139 A | * | 7/1996 | Parker et al. | 382/108 |

(Continued)

FOREIGN PATENT DOCUMENTS

DE 19544187 A1 6/1997
(Continued)

OTHER PUBLICATIONS

Shimmins J. et al.: "The Digitization and Analysis of Thermographic Images", Physics in Medicine and Biology, Taylor and Francis Ltd. London, GB, vol. 22, No. 1, Jan. 1, 1977, pp. 95-97.

(Continued)

*Primary Examiner* — Brian Casler
*Assistant Examiner* — Joel Lamprecht
(74) *Attorney, Agent, or Firm* — The Webb Law Firm

(57) ABSTRACT

An infrared imaging camera (4) acquires a plurality of frames (94) of infrared radiation from a patient (P) positioned in a field-of-view (92) of the camera (4). Each frame (94) is acquired during a corresponding frame sample interval and each frame (94) corresponds to the infrared radiation acquired from an array of optical elements (90) in the field-of-view (92) during its frame sample interval. Plural rates of change are determined from infrared radiation received from the array of optical elements (90), with each rate of change corresponding to a change of infrared radiation received from the same optical element (90) in at least two frames (94). Each rate of change is mapped to a color or a shade of gray and the color or shade of gray of each rate of change is mapped to a position in an image corresponding to the position of the corresponding optical element (90) in the field-of-view (92). The camera (4) can be used for early detection of neoplastic disease process, detection of angiogenesis and/or identification of treatment sites for pain management therapeutic modalities.

21 Claims, 9 Drawing Sheets

U.S. PATENT DOCUMENTS

| | | | |
|---|---|---|---|
| 5,603,328 A | 2/1997 | Zucker et al. | 128/664 |
| 5,692,510 A * | 12/1997 | Gordon et al. | 600/431 |
| 5,803,082 A * | 9/1998 | Stapleton et al. | 600/407 |
| 5,999,843 A * | 12/1999 | Anbar | 600/474 |
| 6,023,637 A * | 2/2000 | Liu et al. | 600/474 |
| 6,081,577 A * | 6/2000 | Webber | 378/23 |
| 6,216,540 B1 * | 4/2001 | Nelson et al. | 73/633 |
| 6,241,672 B1 * | 6/2001 | Hochman et al. | 600/431 |
| 6,246,540 B1 * | 6/2001 | Kabasawa | 360/99.06 |
| 6,381,488 B1 * | 4/2002 | Dickey et al. | 600/474 |
| 6,757,412 B1 * | 6/2004 | Parsons et al. | 382/128 |
| 6,937,885 B1 * | 8/2005 | Lewis et al. | 600/476 |

FOREIGN PATENT DOCUMENTS

| | | |
|---|---|---|
| EP | 0885587 A1 | 12/1998 |
| WO | 9846976 | 10/1998 |

OTHER PUBLICATIONS

Kassen F et al.: "Differential-Thermography a Method for the Early Diagnosis of Mammary Carcinomas by On-Line Image Processing", IEEE Transactions on Nuclear Science, IEEE Service Center, New York, NY, US, vol. NS-30, No. 5, Oct. 1, 1983, pp. 3989-3992.

* cited by examiner

METHOD AND APPARATUS FOR HIGH RESOLUTION DYNAMIC DIGITAL INFRARED IMAGING

BACKGROUND OF THE INVENTION

Heretofore, infrared imaging, sometimes referred to as thermal imaging, has been utilized for non-destructive testing of materials such as printed circuit boards and turbine blades. Application of infrared imaging in medical diagnosis has been limited largely because of inadequate equipment and lack of a general theory relating to the radiation of infrared energy by living animals to the underlying physiological processes responsible for such radiation.

Early use of infrared imaging depended upon detectors that lacked sufficient resolution to be of sufficient and reliable value for medical diagnosis. Notwithstanding improvements in infrared detector technology, the use of infrared imaging cameras to detect fine variations in the surface temperature of a body does not produce data having sufficient information for effective medical diagnosis.

It is, therefore, an object of the present invention to provide an infrared imaging system and a method of using such an infrared imaging system to detect changes in the character of infrared radiation emitted from a body subject to thermal stress, and to obtain diagnostic information about the physiological function of the body from the response of such body to thermal stress. It is an object of the present invention to provide an infrared imaging system which can stereoscopically observe and analyze infrared radiation emanating from a body. Still other objects of the present invention will become apparent to those of ordinary skill in the art upon reading and understanding the following detailed description.

SUMMARY OF THE INVENTION

Accordingly, we have invented a method of producing infrared images of a patient. The method includes providing an infrared imaging camera configured to receive infrared radiation from an array of optical elements in a field-of-view viewable by the infrared imaging camera. A plurality of frames of infrared radiation are acquired from a patient positioned in the field-of-view. Each frame is acquired during a corresponding frame sample interval and each frame corresponds to the infrared radiation acquired from the array of optical elements during its frame sample interval. Plural rates of change of infrared radiation received from the array can be determined, with each rate of change corresponding to a change of infrared radiation received from the same optical element in at least two frames. Each rate of change can be mapped to a color or a shade of gray and the color or the shade of gray of each rate of change can be mapped to a position in an image corresponding to the position of the corresponding optical element in the field-of-view.

The plurality of frames are acquired over an imaging interval and the acquisition occurrence of each frame can be fixed or variable. The infrared radiation received at each optical element can be adjusted for absolute temperature and determining each rate of change can include determining a first derivative or a second derivative. Infrared radiation can be sequentially acquired from each optical element in the field-of-view during the frame sample interval. Alternatively, infrared radiation can be acquired from all of the optical elements in the field-of-view at substantially the same time.

Prior to initiating the acquisition of frames, the patient can be exposed to ambient temperature air. Thereafter, the acquisition of frames can be initiated and the patient can be exposed to a flow of conditioned air at a temperature different than the ambient temperature. The acquisition of frames can be terminated after the imaging interval. At least one marker having an emissivity different than the emissivity of the patient can be positioned on the patient and in the field-of-view. Preferably, the at least one marker is positioned on a fixed anatomical location of the patient.

One or more mirrors can be positioned in the field-of-view adjacent the patient. The one or more mirrors can be oriented to reflect infrared radiation from a part of the patient that is within the field-of-view but is concealed from the infrared imaging camera by another part of the patient.

A grid can be positioned between the infrared imaging camera and the patient. Thermal energy can be conveyed to the patient through the grid and a frame of infrared radiation can be acquired directly from the patient and from the one or more mirrors. A three-dimensional image of the patient can be constructed from the infrared radiation acquired directly from the patient and acquired from the one or more mirrors.

We have also invented an infrared imaging apparatus. The imaging apparatus includes a means for detecting infrared radiation from each optical element of an array of optical elements forming a field-of-view of the imaging apparatus. A controller is connected for controlling the means for detecting to selectively acquire a plurality of frames of infrared radiation from the array at a like plurality of sample intervals. Each frame corresponds to the infrared radiation acquired from all of the optical elements of the array during one sample interval. A workstation determines plural rates of change of the infrared radiation received by the means for detecting from the array. Each rate of change corresponds to a change of infrared radiation acquired from like optical elements in at least two frames. The workstation maps each rate of change to a color or shade of gray and the workstation maps the color or the shade of gray of each rate of change to a position in an image corresponding to the position of the corresponding optical elements in the field-of-view.

Preferably, each optical element corresponds to the smallest element in the field-of-view that can be processed by the means for detecting.

The imaging apparatus can include means for converting infrared radiation acquired from each optical element into corresponding data. The workstation determines the rate of change for like optical elements in at least two frames from the data corresponding to the infrared radiation acquired from each optical element of each frame.

Preferably, the acquisition occurrence of each of the plurality of frames occurs logarithmically over an imaging interval and the acquisition occurrence increases late in the imaging interval.

The acquisition of frames can be synchronized to heartbeat cycles of a patient received in the field-of-view. The at least two frames can be acquired during a like portion of different heartbeat cycles.

DETAILED DESCRIPTION OF THE PREFERRED EMBODIMENTS

Figure 1:
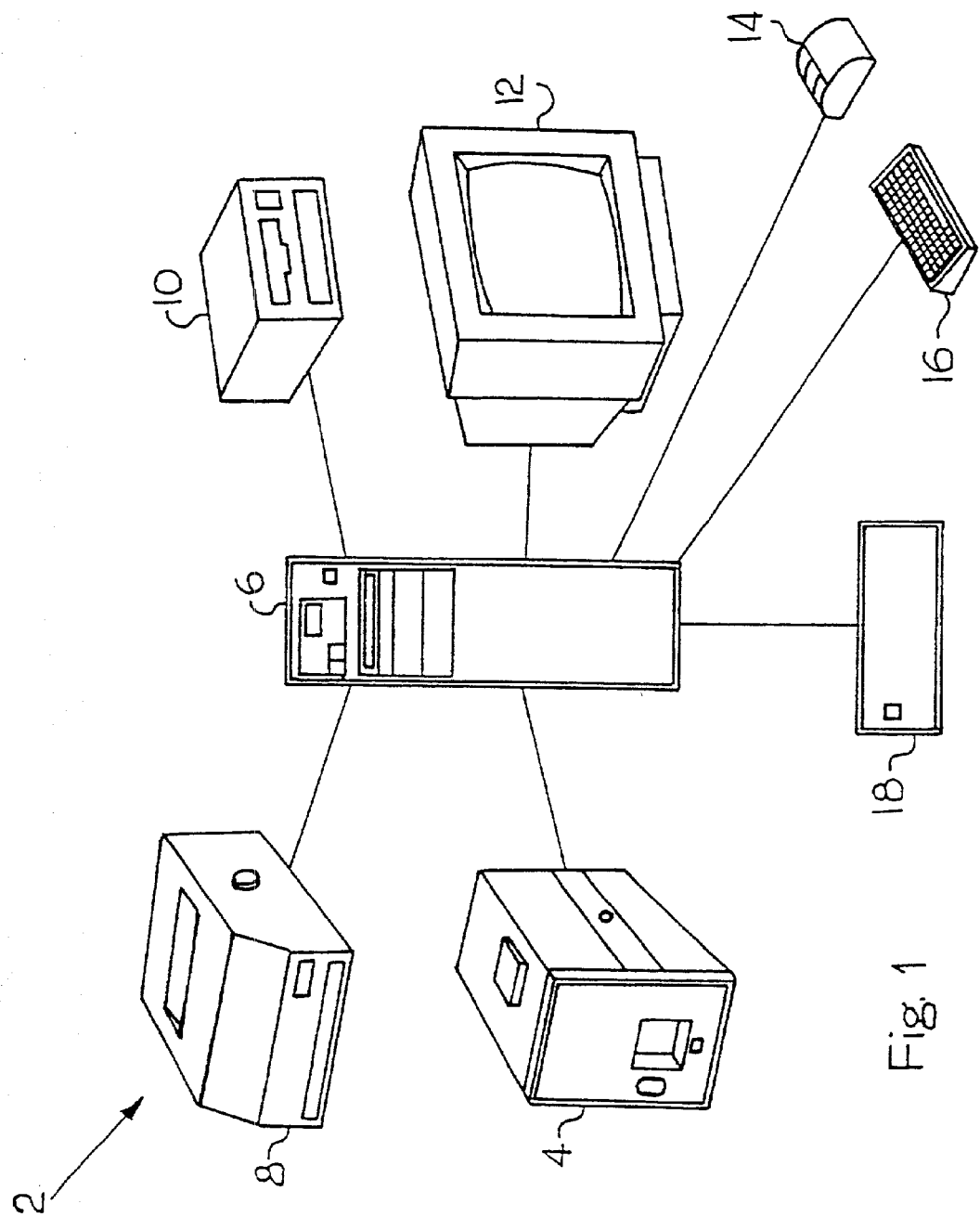
FIG. 1 is a block diagram drawing of an infrared imaging system including an infrared imaging camera.

With reference to FIG. 1, an infrared (IR) imaging system 2 includes an IR imaging camera 4 connected to a workstation 6. IR imaging camera 4 receives command signals from workstation 6 and supplies to workstation 6 quantitative data and information about the IR radiation received by IR imaging camera 4. Also connected to workstation 6 is a printer 8, a storage 10, a display 12, a pointing device 14, a keyboard 16 and a power conditioner 18 which are used by a user of IR imaging system 2 in a manner known in the art.

Figure 2:
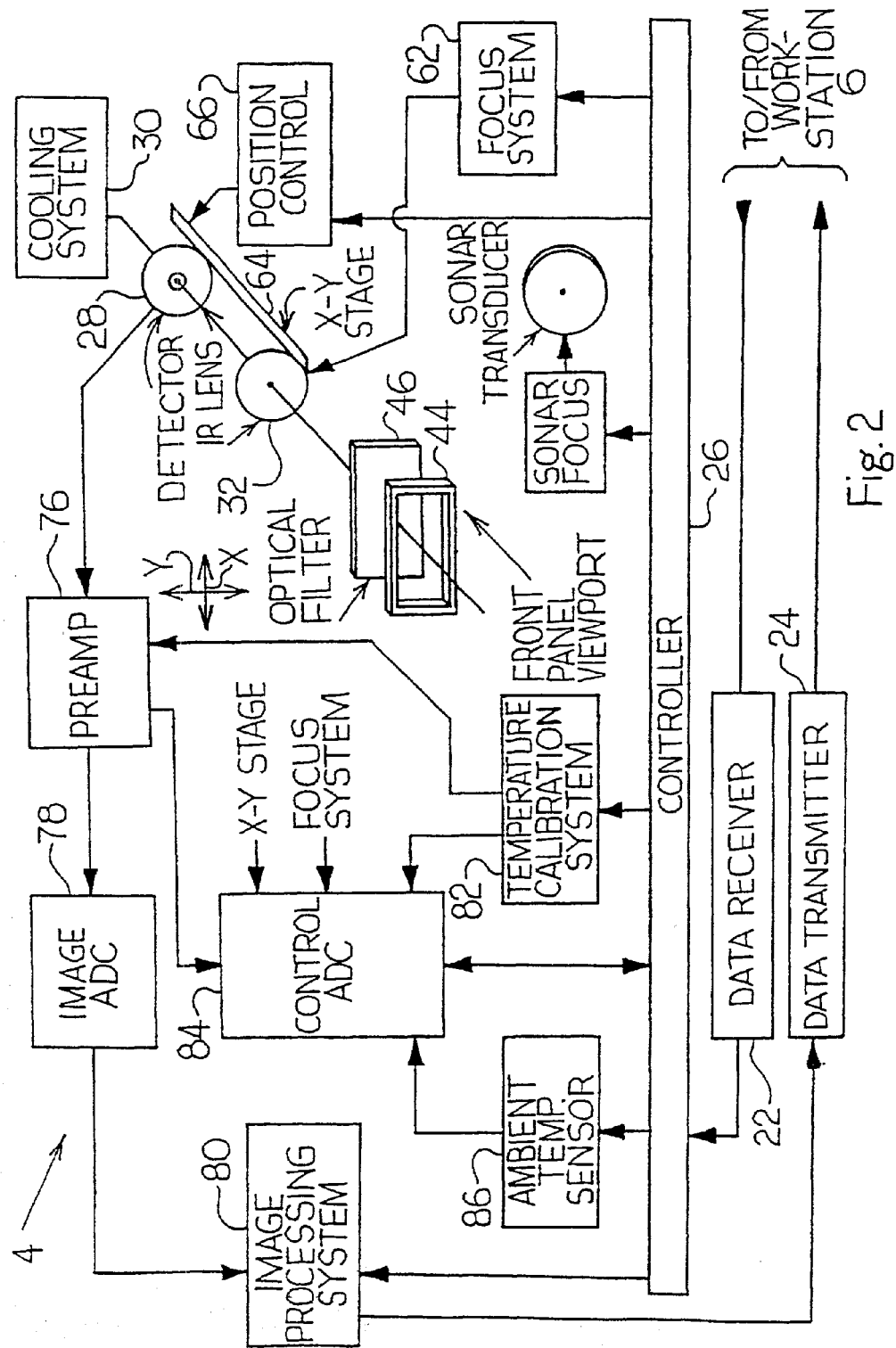
FIG. 2 is a block diagram drawing of the infrared imaging camera of FIG. 1 including a single, selectively positionable infrared detector.

With reference to FIG. 2, and with continuing reference to FIG. 1, IR imaging camera 4 includes a data receiver 22 and a data transmitter 24 for communicating with workstation 6. A controller 26 operating under the control of a software program is connected to receive data from data receiver 22. IR imaging camera 4 includes a detector 28 connected to a cooling system 30 for cooling detector 28 to an acceptable operational temperature in a manner known in the art. Detector 28 receives IR radiation from an IR lens 32 which focuses IR radiation received thereby onto detector 28. Prior to reaching IR lens 32, IR radiation passes through a front panel viewport 44, and in certain cases, an optical filter 46.

A focus system 62 for focusing IR lens 32 is connected to receive control signals from controller 26. Under the control of controller 26, the optical focus and/or zoom of IR lens 32 can be adjusted via focus system 62 by means well-known to modern digital photographic systems.

A motorized X-Y positioning stage 64 is connected to IR lens 32 and detector 28 for controlling the direction from which IR lens 32 and detector 28 detect IR radiation propagating thereto from optical filter 46. A position control 66 is connected to receive control signals from controller 26. Under the control of controller 26, position control 66 controls the position of X-Y stage 64 so that IR lens 32 and detector 28 can be selectively positioned to detect beams of IR radiation propagating thereto from select parts of optical filter 46.

A preamplifier 76 is connected to receive from detector 28 signals corresponding to the intensity of IR radiation received thereby. Preamplifier 76 amplifies and filters each signal output by detector 28 and supplies each amplified and filtered signal to an image analog-to-digital converter (ADC) 78 which converts each amplified and filtered signal from preamplifier 76 into a corresponding digital signal which is supplied to an image processing system 80, such as a gate array. Operating under the control of controller 26, image processing system 80 supplies IR radiation data and information to data transmitter 24 for transmission to workstation 6.

Preamplifier 76 is preferably connected to receive data and information about absolute temperature from a temperature calibration system 82. Under the control of controller 26, temperature calibration system 82 provides absolute temperature calibration data to preamplifier 76. Preamplifier 76 combines the absolute temperature calibration data from temperature calibration system 82 with each signal output by detector 28 to adjust the amplified and filtered signal output by preamplifier 76 for the absolute temperature of the IR radiation received by detector 28.

A control ADC 84 is connected to receive analog signals output from focus system 62, X-Y stage 64, temperature calibration system 82, preamplifier 76 and an ambient temperature sensor 86. Under the control of controller 26, control ADC 84 selectively supplies to controller 26 digital signals corresponding to the analog signals received by control ADC 84. The digital signals received by controller 26 from control ADC 84 are used by controller 26 to control the operation of IR imaging camera 4.

Figure 3:
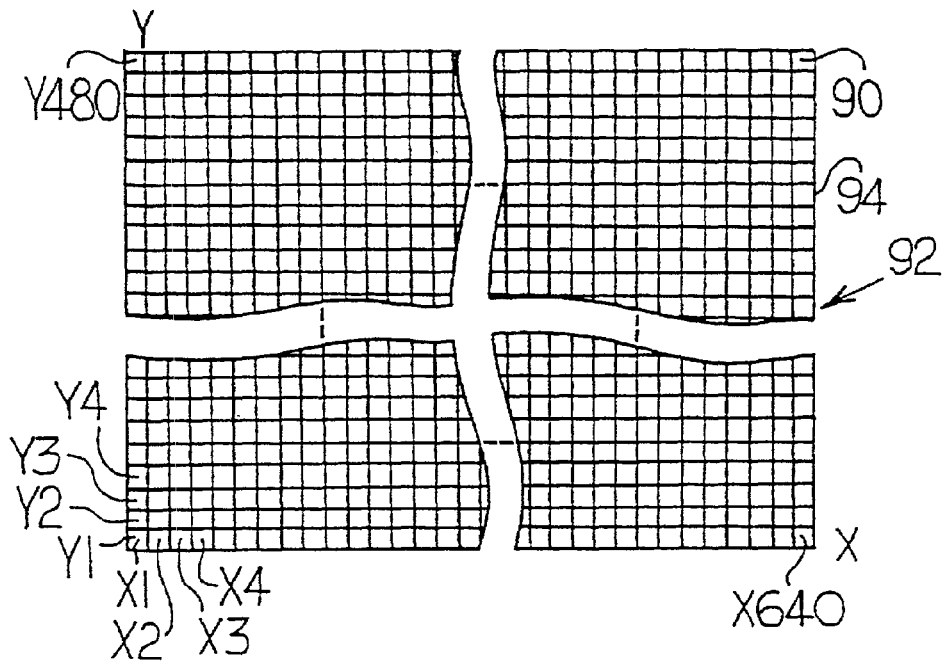
FIG. 3 is a schematic drawing of a frame representing the total field-of-view (tFOV) viewable by the infrared imaging camera of FIG. 2 including an array of optical elements forming the frame.

With reference to FIG. 3, and with continuing reference to FIGS. 1 and 2, controller 26 controls the sampling of IR radiation by detector 28, the focus of IR lens 32 and the position of X-Y stage 64 as required to receive and record IR radiation from each optical element (optel) 90 in an array of optical elements (optels) 90 in a total field-of-view (tFOV) 92 viewable by IR imaging camera 4. As used herein, the terms "optical element" or "optel" refer to the smallest element in tFOV 92 that can be individually processed in an instantaneous field-of-view (iFOV) of detector 28.

In operation, IR imaging camera 4 obtains IR radiation from each optel 90 in tFOV 92. For example, starting with the optel 90 at position X1,Y1 in tFOV 92 shown in FIG. 3, controller 26 controls X-Y stage 64, detector 28 and IR lens 32 to acquire IR radiation from each optel 90 along the horizontal X-axis for a fixed vertical Y-axis displacement. Specifically, IR imaging camera 4 acquires IR radiation from each optel 90 between position X1,Y1 and position X640,Y1 inclusive in tFOV 92. Next, IR imaging system 2 adjusts the position of the X-Y stage 64 so that detector 28 acquires IR radiation from each optel 90 between position X1,Y2 and position X640,Y2 inclusive in tFOV 92. IR imaging camera 4 continues scanning the optels 90 in tFOV 92 in this manner until all the optels 90 forming tFOV 92 have been acquired.

Since IR imaging camera 4 shown in FIG. 2 has a single detector 28, IR imaging camera 4 necessarily obtains information from the optel 90 at each position in tFOV 92 over a discreet period of time. The interval between sampling the optel 90 at position X1,Y1 and sampling the optel 90 at position X640,Y480 in tFOV 92, i.e., the frame sample interval, is determined by the rate of change of IR radiation received from an object being imaged. In this respect, the frame sample interval can be adjusted as a function of the rate of change of IR radiation received from the object being imaged. Preferably, IR imaging camera 4 samples the optel 90 at each position in tFOV 92 a plurality of times per frame sample interval and averages the samples for each optel 90 at every position in tFOV 92 to obtain an average of the IR radiation received from each optel 90 which is utilized in a manner to be described hereinafter. In the case of a photoconductive detector, the information from such sampling (voltage output) is summed while in the case of a photovoltaic detector, the information (current output) is integrated.

Image ADC 78 determines a digital value for the absolute temperature of the instantaneous or average IR radiation detected by detector 28 for the optel 90 at each position in tFOV 92. Next, image processing system 80 arranges the digital values obtained for the optel 90 at each position in tFOV 92 during the frame scan interval into a frame 94. The digital value associated with each optel 90 of a frame 94 preferably represents the absolute temperature of the IR radiation received by detector 28 from the particular location on the object being imaged over the corresponding frame sample interval.

Figure 4:
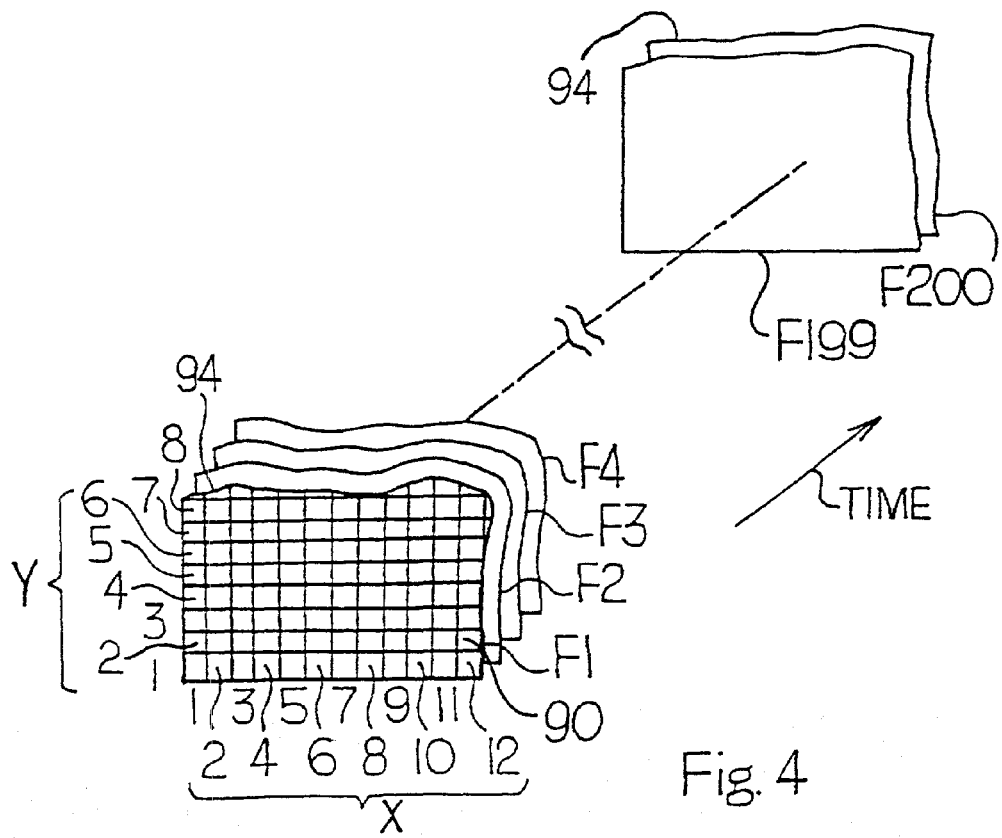
FIG. 4 is a schematic drawing of a plurality of frames of temperature vs. time obtained using the infrared imaging camera of FIG. 2.

With reference to FIG. 4, and with continuing reference to all previous Figures, IR imaging camera 4 obtains a plurality of frames, e.g., F1-F200, of the object being imaged over an imaging interval, e.g., five minutes. When each frame 94 is received and assembled in image processing system 80, controller 26 causes each frame 94 to be transferred from image processing system 80 to workstation 6 via data transmitter 24. In medical applications, it is preferred that acquisition of each of the plurality of frames 94 occurs logarithmically over the imaging interval, with increasing acquisition occurrence of adjacent frames 94 occurring late in the imaging interval. However, the acquisition of adjacent frames 94 can be fixed or varied in any desired manner.

Figure 5:
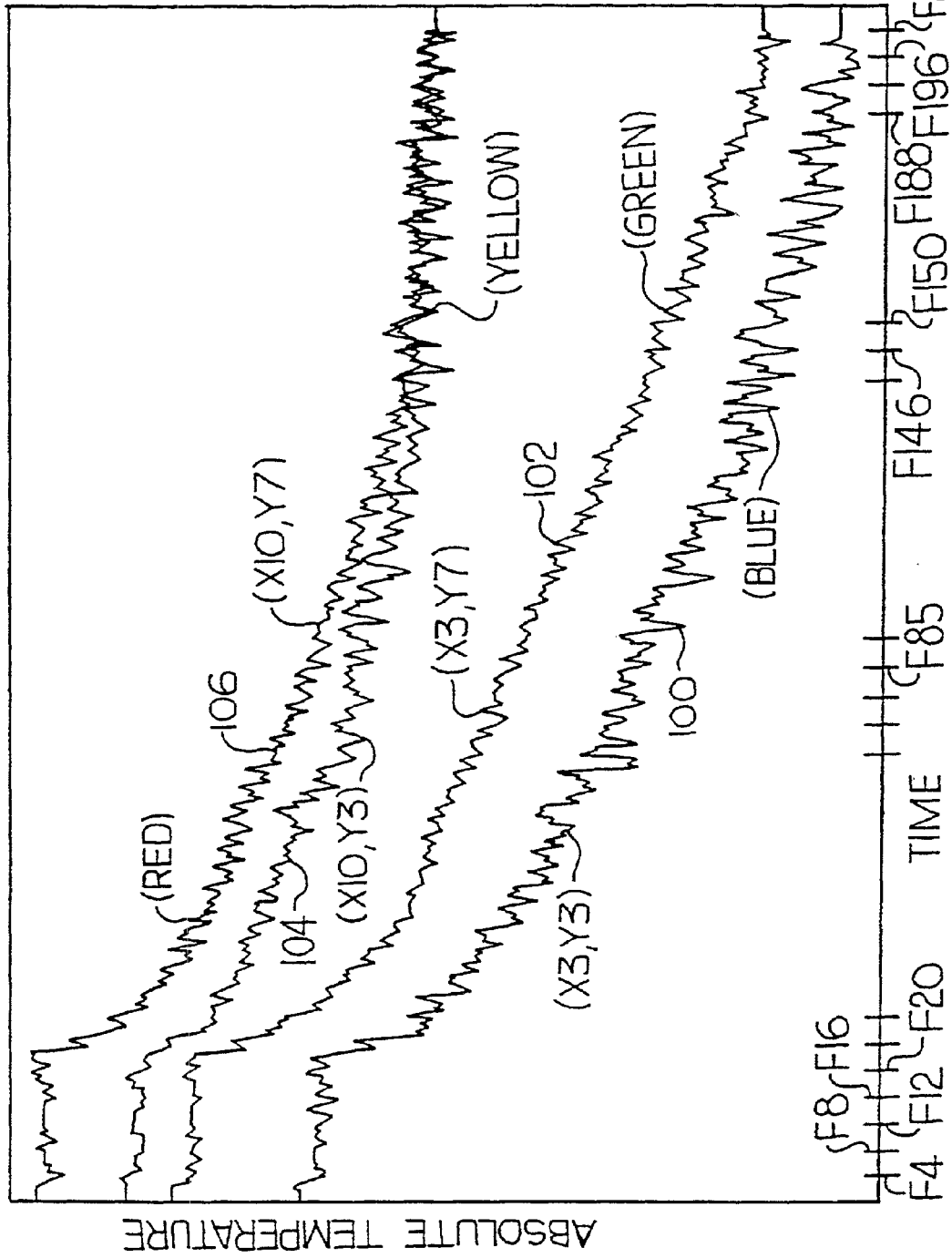
FIG. 5 is a chart of temperature vs. time curves determined from infrared radiation received by four like optical elements from each of the plurality of frames shown in FIG. 4.

With reference to FIG. 5, and with continuing reference to all previous Figures, for purpose of illustration, the temperature acquired for like optels 90 of each frame 94 can be shown as temperature-time curves, e.g., curves 100-106. When the plurality of frames 94 has been acquired over the imaging interval, workstation 6 determines for like optels 90 in each frame 94 a first rate of change, i.e., the first derivative, for each temperature-time curve and/or a second rate of change, i.e., the second derivative, for each temperature-time curve. For example, temperature-time curve 100 shows temperature vs. time for optel 90 at position X3,Y3 for frames F1-F200 shown in FIG. 4. Similarly, temperature-time curves 102, 104 and 106 show temperature vs. time for the optels 90 at positions X3,Y7; X10,Y3; and X10,Y7 for frames F1-F200 shown in FIG. 4. Workstation 6 can determine the first and/or second rates of change of the temperature-time curves, e.g., 100, 102, 104 and 106, from the optels 90 at like positions in each frame 94, or from some select plurality of frames 94, e.g., frames F85-F150.

Workstation 6 maps the first rate of change and/or the second rate of change for each temperature-time curve, e.g., 100-106, to a unique color for display purposes. Preferably, in medical applications for early identification of neoplastic activity in the breast, the color blue is mapped to the curve having the greatest first rate of change and/or second rate of change and the color red is mapped to the curve having the smallest or least first rate of change and/or second rate of change. Curves having first and/or second rates of change between the greatest and the least first and/or second rates of change are mapped to colors between red and blue. For example, between frame F85 and frame F150 in FIG. 5, workstation 6 maps the color blue to temperature-time curve 100 having the greatest first and/or second rate of change; maps the color green to temperature-time curve 102; maps the color yellow to temperature-time curve 104; and maps the color red to temperature-time curve 106 having the least first and/or second rate of change.

Next, workstation 6 maps the position of each optel 90 or group of optels 90 in tFOV 92 to a corresponding pixel or group of pixels on display 12. When a color is mapped to the first and/or second rate of change of a portion or all of each temperature-time curve, e.g., 100-106, workstation 6 causes the mapped color of the first rate of change or the second rate of change of each temperature-time curve to be displayed on display 12 on the pixel having the position corresponding to the position of the corresponding optel 90 in tFOV 92. The colors thus mapped to display 12 form thereon a color slope map image of the first rate of change or the second rate of change.

Alternatively, workstation 6 can map each temperature-time curve over some select plurality of frames 94 to a gray scale of the first and/or second rate of change thereby forming a gray scale slope map image. Preferably, the gray scale extends between the greatest or least first or second rate of change for the color white and the other of the greatest or least first or second rate of change for the color black. Workstation 6 can also map each curve over some select plurality of frames 94 having a first or second rate of change less than or greater than predetermined first or second rate of change to the gray scale and can map each curve over the same select plurality of frames 94 having a first or second rate of change the other of less than and greater than the predetermined first or second rate of change to one or more colors thereby producing a mixed gray scale and color slope map image. Moreover, the data in each frame 94 or selected pluralities of frames 94 can be filtered and amplified, in a manner known in the art, to enhance detail of the gray scale and/or color slope map image.

The present invention finds particular application in early detection of breast cancer and, more particularly, in detection of recent angiogenesis associated with maturing neoplastic processes in the breast. Specifically, it is well-known that as breast cancer develops, a process known as angiogenesis occurs and a neoplastic lesion or nascent tumor develops an independent blood supply. It has been observed that blood vessels formed by recent angiogenesis are not responsive to the body's sympathetic or autonomic nervous system. Hence, in response to exogenous thermal stress, areas within the body supplied with blood as a result of recent angiogenesis exhibit response to thermal stress inconsistent with the response of adjacent areas within the same organ of the body, the blood supply of which is not the result of recent angiogenesis. The IR radiation emitted over time from areas of the skin can be mapped to underlying physiological, biochemical and neurological processes at a variety of structural and systemic organizational levels, e.g., cells, tissues, organs and/or systems. IR radiation from those areas of the skin associated with areas of recent angiogenic activity within the body can be shown to be significantly different when compared to the IR radiation from those skin areas of the body having a blood supply not associated with recent angiogenesis.

Using IR imaging system 2, the above-described method of obtaining temperature-time curves and information about the first and/or second rates of change of each temperature-time curve, the present invention can identify the existence of recent angiogenesis and provide meaningful data on the location of such angiogenesis within the breast thereby providing an early indication that an active neoplastic process may be underway in a patient or the patient may have already contracted cancer.

An additional application of the invention applies mathematical and statistical methods to examine IR radiation emanating from the skin for the purpose of identifying anigosomes or thermatomes as well as anomalous areas of statistically significant excess or deficiency of IR radiation which can be mapped to underlying physiological, biochemical and neurological processes at a variety of organizational levels, e.g., cells, tissues, organs and/or systems. This information is of special value in the treatment of chronic pain, particularly myofascial pain, by means of alternative therapies, such as acupuncture, acupressure, or application of exogenous electromagnetic radiation, such as therapeutic infrared or radiofrequency energy.

Application of the invention for the purpose of identifying angiosomes and thermatomes permits practitioners of "Western" medicine, to efficiently utilize the therapeutic techniques of "Eastern" or "Oriental" medicine, such as acupuncture and acupressure, and permits the practitioners of "Eastern" or "Oriental" medicine to communicate their insights and techniques to "Western" health care providers.

Figure 6:
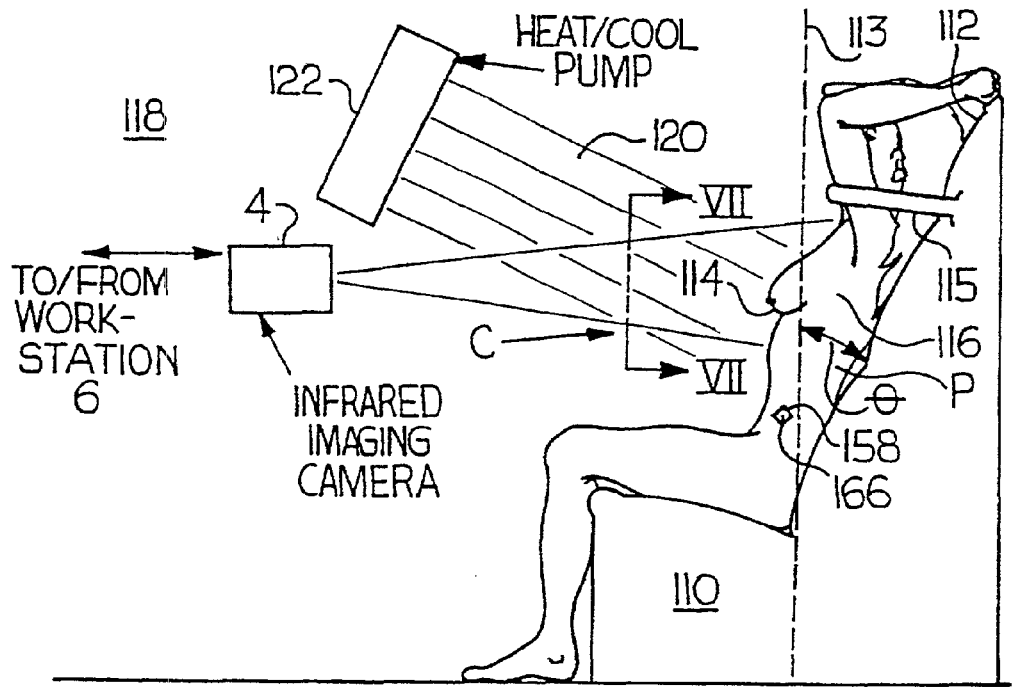
FIG. 6 is a schematic drawing of the infrared imaging camera of FIG. 2 positioned to acquire frames of infrared images from a patient exposed to thermal stress by a heat/cold pump.

With reference to FIG. 6, and with continuing reference to all previous Figures, the present invention will now be described with reference to acquiring information from IR radiation received from a patient P during examination of breasts 114. Preferably, patient P sits on a bench or chair 110 having a back 112 which reclines at an angle θ from a vertical axis 113 or patient P stands and leans against a similarly angled leaning board (not shown). Angle θ is selected so that the underside of each breast 114 is within tFOV 92 of IR imaging camera 4. To facilitate IR imaging of the lateral area of the breasts 114 and the axilla region, patient P moves her arms laterally and cephally away from her body, resting her elbows and forearms on supports 115. IR imaging camera 4 is positioned in spaced relation to patient P so that the entire anterior chest area C of patient P and, more particularly, breasts 114 of patient P are within tFOV 92 of IR imaging camera 4. Preferably, IR imaging camera 4 is positioned so that breasts 114 and adjacent torso 116 of patient P fill a majority of tFOV 92. However, IR lens 32 can be adjusted to optically zoom on a specific defined area of patient P thereby enabling acquisition of IR radiation from this selected area.

In the present invention, optical zoom using IR lens 32 isolates the acquisition of IR radiation from a selected area of patient P, but does not increase the surface area of patient P viewed by each optel 90. It is believed that acquisition of IR images over a smaller array of optels 90 by optical zoom will improve resolution of the image in the subset of the portion of patient P being imaged.

The distance between patient P and IR imaging camera 4 is selected as a tradeoff between the focal length of IR lens 32 and the area of patient P which must be within tFOV 92 in order to obtain meaningful physiological information. To this end, IR lens 32 is preferably configured so that all of the portion of patient P being imaged in tFOV 92 is in focus. Preferably, IR lens 32 of IR imaging camera 4 is configured to have a long focal length along with a blur circle and a diffraction limit less than the size of each optel 90 viewable by detector 28. With this combination, IR imaging camera 4 has a depth-of-field that enables each portion of patient P in tFOV 92 to be in focus regardless of the distance each sub-portion of patient P is spaced from IR imaging camera 4.

Patient P and bench 110 are received in a room 118 having an ambient temperature which is comfortable for patient P when disrobed. At a suitable time after patient P is received on bench 110, IR imaging camera 4 initiates acquisition of frames 94 of digital values corresponding to absolute temperature represented by IR radiation received from patient P in the absence of thermal stress to patient P. The number of frames and length of time required to acquire sufficient "baseline" information before application of exogenous thermal stress is determined either by a human operator or automatically by computer analysis of acquired data. After obtaining a desired number of frames 94 in the absence of thermal stress, patient P is exposed to a flow of conditioned air 120 from one or more heat/cold pumps 122 positioned in front of patient P. The one or more heat/cold pumps 122 are positioned to provide a substantially uniform flow of conditioned air 120 to cool or, under certain examination protocols, warm the portion of patient P in tFOV 92 at a substantially constant rate. Preferably, a temperature of the cool flow of conditioned air 120 supplied to patient P from heat/cold pump 122 is different than the ambient temperature of room 118, but still comfortable to patient P. It has been observed that a temperature of the flow of conditioned air 120 which is only 10° F. less than ambient room temperature produces in patient P a desired sympathetic response.

Under certain clinical conditions, however, it is appropriate to warm each breast 114 before cooling in order to promote more blood flow to the surface of the skin and assure that patient P is not already vasoconstricted as a result of ambient environment conditions. Additional meaningful information can be obtained from the IR radiation received from patient P in response to alterations in thermal stress, e.g., warming to cooling and cooling to warming. These alterations in thermal stress can induce a kind of physiological hysteresis in the IR radiation emissions of particular skin areas associated with certain physiological processes in underlying tissues and organs.

For example, heat/cool pump 122 initially supplies to patient P a flow of conditioned air 120 and IR imaging camera 2 acquires a plurality of frames 94 of breasts 114 of patient P. Certain underlying physiological processes manifest changes in IR radiation from the areas of the skin associated with such processes during the warming/cooling cycle, leading to a statistically significant difference in the first and/or second rate of change of IR radiation received from optels 90 associated with these specific areas vs. the first and/or second rate of change of the IR radiation received from optels 90 associated with less responsive tissue. This difference in the first and/or second rate of change can be displayed on display 12 as a difference in the gray scale and/or color slope map image. A three-dimensional image of the underlying structures and systems can also be developed from the acquired data.

As a result of tissue characteristics and properties akin to that of hysteresis associated with certain magnetic materials, thermal stress consisting of warming followed by cooling, a "hot and cold" cycle, and/or cooling followed by warming, a "cold and hot" cycle, enhances the ability of the IR imaging system 2 to identify areas of tissue associated with recent angiogenic activity, such as in breasts 114 of patient P.

Figure 7:
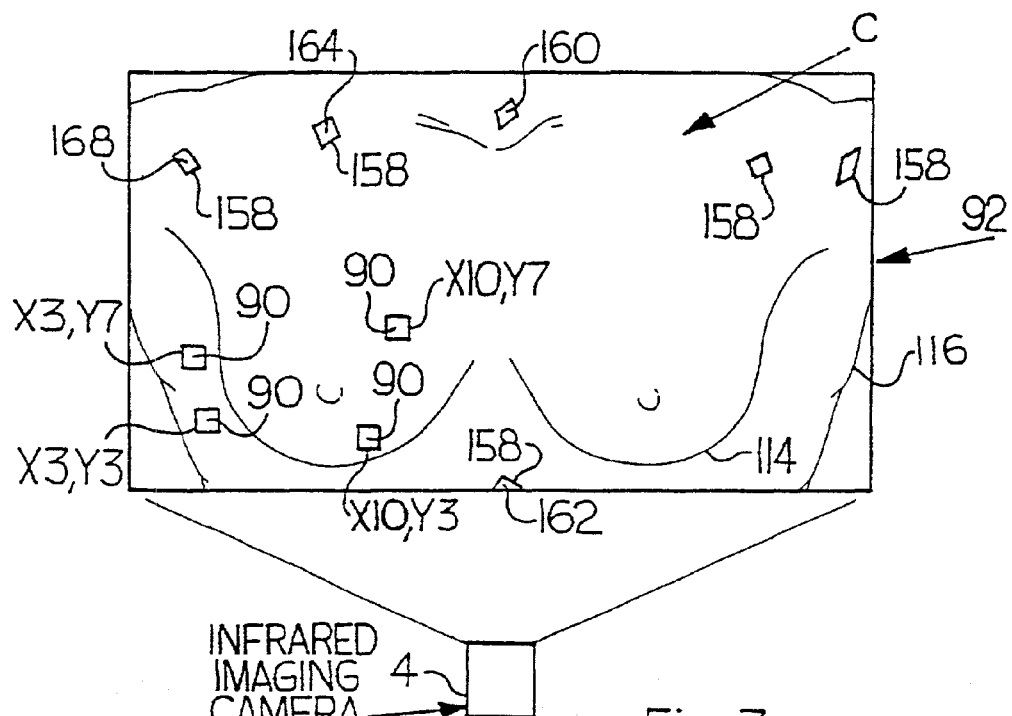
FIG. 7 is a view of the patient in FIG. 6 taken along lines VII-VII including on the patient the position of the four optical elements in the field-of-view from which infrared radiation is acquired to generate the temperature vs. time curves shown in FIG. 5.

In response to receiving a flow of cool conditioned air 120 from heat/cold pump 122, the sympathetic nervous system of patient P limits blood flow to the skin surface area of patient P being cooled. It has however, observed, that the sympathetic nervous system does not limit blood flow to tissue of patient P which has experienced recent angiogenesis or is experiencing the onset of angiogenesis. Thus, IR radiation from those areas of the skin of patient P associated with those tissues or organs whose blood supply is associated with recent angiogenesis or ongoing angiogenic activity does not react to the cool flow of conditioned air 120 in the same manner as other tissues of patient P. For example, as shown in FIGS. 5 and 7, the skin surface area of patient P viewed at the optel 90 at position X3,Y3 of tFOV 92 produces temperature-time curve 100 between frame F24 and frame F200 in response to cooling of patient P by the cool flow of conditioned air 120. Similarly, cooling of patient P with the cool flow of conditioned air 120 causes the skin surface area of patient P viewed at the optels 90 at positions X3,Y7; X10,Y3; and X10,Y7 between frame F24 and frame F200 to produce temperature-time curves 102, 104 and 106, respectively.

As shown in FIG. 5, between frames F85 and F150, curves 104 and 106 exhibit lesser first and second rates of change than curves 100 and 102. This difference in first and second rates of change indicates that the skin surface areas of patient P viewed at the optels 90 at positions X10,Y3 and X10,Y7 is not as responsive to cooling by the flow of cool conditioned air 120 as the skin surface area of patient P viewed at the optels 90 at positions X3,Y3 and X3,Y7. This provides an indication that the tissues of patient P in tFOV 92 may be experiencing the onset of angiogenesis or may already be supplied with blood as a result of recent angiogenesis.

In addition to providing information about angiogenesis and angiogenic activity, the present invention can also provide meaningful information about the activity of any tissue, organ, or physiological system, the blood flow of which is regulated by the sympathetic nervous system.

Preferably, in the special case of early detection of neoplastic disease in the human breast, the starting frame 94, e.g., frame F85, and the number of frames 94 utilized for detecting the first and/or second rates of change of the temperature-time curves for the optel 90 at each position in tFOV 92 can be varied as desired for presenting an image on display 12. For example, the first or second rate of change of each temperature-time curve 100, 102, 104 and 106 shown in FIG. 5, are detected between frames F85 and F 150. However, the first or second rate of change of each temperature-time curve 100, 102, 104 and 106 could be determined between frames F100 and F125, between frames F20 and F85, between frames F75 and F175, and so forth as desired.

Moreover, the number of digital bits utilized to map the gray scale and/or colors to the first or second rate of change of each temperature-time curve shown in FIG. 5 can also be varied. For example, if image ADC 78 is a 12-bit analog-to-digital converter, the gray scale and/or color slope map images can be mapped to less than the full 12-bit range of image ADC 78. For example, workstation 6 can map the first or second rate of change of each temperature-time curve shown in FIG. 5 to a range of digital values corresponding to base ten numbers 800-1600, thus eliminating from the immediate display 12 information of little or no immediate diagnostic value, but without losing such information from the patient record maintained in a patient database.

Figure 8B:
FIG. 8b is a gray scale map image of the patient shown in FIG. 8a wherein temperature vs. time curves having slopes greater than the slope of temperature vs. time curves associated with the color red are mapped to a shade of gray according to their slope and the color red is illustrated by a red color symbol.
Figure 8A:
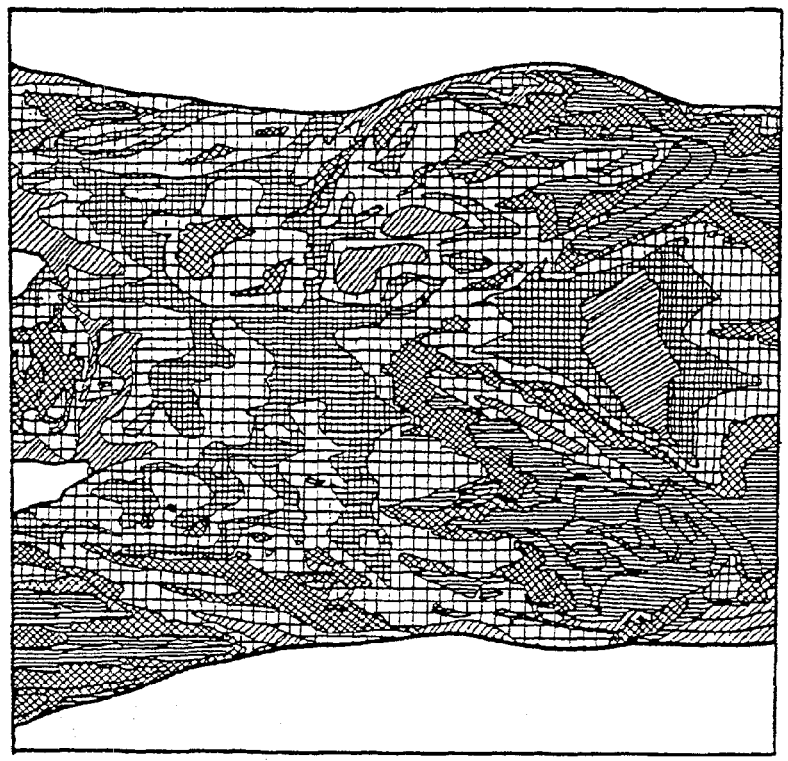
FIG. 8a is a black and white rendering including color symbols to represent the colors of a color slope map image of breasts of a patient wherein each temperature vs. time curve associated with the optical elements at each position in the tFOV over the plurality of frames is mapped to a color related to a rate of change of the slope of the temperature vs. time curve.

FIGS. 8a-8b show a black and white rendering of a color slope map image of patient P's breasts 114 and a combined gray scale and black and white rendered color slope map image of the patient P's breasts 114, respectively. Since the acquisition of frames 94 occurs over the imaging interval, the temperature-time curves represent the IR radiation from the entire tissue mass of patient P's breasts 114 over time, not merely the temperature at the surface of the skin. As can be seen, the color slope map image shown in FIG. 8a provides detailed information regarding the sympathetic response of patient P's breasts 114 to the flow of conditioned air 120 from heat/cold pump 122. In this color slope map image, colors toward the blue end of the spectrum are associated with optels 90 having a greater first or second rate of change, e.g., curve 100 in FIG. 5, and areas shown in red have associated therewith optels 90 having a lesser first or second rate of change, e.g., curve 106 in FIG. 5. The colors green, yellow and orange in the color slope map image shown in FIG. 8a are associated with temperature-time curves having slopes between the slopes of temperature-time curves 100 and 106 of FIG. 5.

In FIG. 8b, areas of tFOV 92 with optels 90 having associated temperature-time curves with first or second rates of change greater than the slope associated with the color red are mapped to a gray scale and temperature-time curves having first or second rates of change corresponding to the color red are shown by a red color symbol. More specifically, the combined gray scale and black and white rendered color slope map image of FIG. 8b is formed by combining a gray slope map image of the last thirty-two frames 94 acquired over the imaging interval and a color slope map image of the same last thirty-two frames 94. The gray scale image is formed by high-pass filtering for each frame 94 the digital value associated with each optel 90. The second rate of change is determined for the thus filtered digital values of like optels 90 in each of the last thirty-two frames and the thus determined second rates of change are mapped to a gray scale to form the gray scale map image portion of FIG. 8b. The second rate of change for like optels is also mapped to colors, with the color red mapped to second rates of change having the least rate of change to form a color slope map image. Optels 90 of the color slope map image associated with the color red replace like optels 90 in the gray scale map image and the thus created gray scale/color slope image is displayed on display 12 to produce the gray scale/color slope image of FIG. 8b. The areas shown by a red color symbol in FIG. 8b are associated with tissue where recent angiogenic activity or angiogenesis has occurred or may be occurring and, therefore, such tissue may require further investigation.

Figure 9:
FIG. 9 is a gray scale map image of breasts of another patient having jagged vasculature.

The combined gray scale and black and white rendered color slope map image of FIG. 8b also clearly illustrates the vascular structure within patient P's breasts 114 providing further information of diagnostic value to the physician. It has been noted empirically that breasts 114 which exhibit a complex or highly irregular vascular structure such as shown in FIG. 9, is considered suspicious and indicates that this patient P is at greater risk for contracting breast cancer than if the vascular structure were more regular. By virtue of being able to detect and display the vascular structure of breasts 114 in some detail, the present invention makes possible early detection of processes such as angiogenesis associated with neoplastic disease such as breast cancer, and the anatomical structures or physiological features which represent risk factors associated with neoplastic disease such as breast cancer, thereby permitting patient P to take some action, such as elimination of "life style" risk factors, long before a tumor is palpable and at a time when changes a patient P may undertake in their personal lifestyle may prevent development of breast cancer.

The present invention can also be utilized to determine patient P's blood flow by comparing, frames 94 acquired at like times over a plurality of "heartbeat" cycles. Specifically, the acquisition by IR imaging camera 4 of each frame 94 can be synchronized to specific portions of a patient P's heartbeat cycle. For example, frames F1, F6, F11, etc., are acquired during a P wave of each of a plurality of heartbeat cycles; frames F2, F7, F12, etc., are acquired during a Q wave of each of the plurality of the same heartbeat cycles; frames F3, F8, F13, etc., are acquired during an R wave of each of the plurality of the same heartbeat cycles; frames F4, F9, F14, etc., are acquired during an S wave of each of the plurality of the same heartbeat cycles; and frames F5, F10, F15, etc., are acquired during a T wave of each of the plurality of the same heartbeat cycles. Utilizing elements of the patient P's own heartbeat cycles as a "time code" throughout the entire image acquisition series permits more efficient application of mathematical methods of image processing and analysis with increased accuracy. Moreover, the use of a well-defined electrophysiological process, such as the heartbeat, with a well-established graphical display representation, e.g., an electrocardiogram, enhances the comparison with image series obtained during different examinations and improves the efficiency of statistical analysis of data acquired over multiple examinations of the same or different patients.

When a desired plurality of frames 94 have been acquired over a desired plurality of heartbeat cycles, workstation 6 determines for like optels 90 in frames 94 associated with a particular moment in each heartbeat cycle a first rate of change and/or a second rate of change. For example, workstation 6 determines a first and/or second rate of change for like optels 90 in frames F1, F6, F11, etc., i.e., frames acquired during P waves of the plurality of heartbeat cycles; determines a first and/or second rate of change for like optels 90 in frames F2, F7, F12, etc., i.e., frames acquired during Q waves of the plurality of heartbeat cycles; and so forth for like optels 90 in frames acquired during R waves, S waves and T waves of the plurality of heartbeat cycles.

Workstation 6 maps the first rate of change and/or the second rate of change for like optels 90 in frames 94 acquired during like moments of the plurality of heartbeat cycles to a shade of gray and/or color in the above-described manner. Workstation 6 causes the thus mapped shades of gray and/or color to be displayed on the pixel or group of pixels of display 12 having positions corresponding to the position of the corresponding optel or optels 90 in tFOV 92 to form a gray scale and/or color slope map image of the first and/or second rate of change during a like moment of a plurality of heartbeat cycles. For example, workstation 6 maps a shade of gray and/or color to the first and/or second rates of change of like optels 90 in frames F1, F6, F11, etc., and displays on display 12 a gray scale and/or color slope map image corresponding to the patient P's blood flow during the P wave of plurality of heartbeat cycles. Similarly, workstation 6 maps a shade of gray and/or color to the first and/or second rates of change of like optels 90 in frames 94 associated with the Q wave, R wave, S wave or T wave of a plurality of the patient P's heartbeat cycles and selectively displays on display 12 the gray scale and/or color slope map image thereof.

Isolating frames 94 associated with like moments of a plurality of heartbeat cycles enables correlation between differences in IR radiation from the skin surface of the patient P and blood flow at multiple levels and locations throughout the tissues of interest thereby permitting quantitative assessment of blood flow in the patient P's body in tFOV 92 of IR imaging camera 4, and providing further diagnostic information of value to the physician. Utilization of a reliable consistent time code marker, such as the patient P's own heartbeat, permits application of mathematical processes for image enhancement and increases the overall resolution of the entire imaging system improving both the sensitivity and selectivity of the system as a means of identifying, characterizing and evaluating complex sympathetically mediated physiological processes within the living human body and the bodies of other animals.

The present invention can also be utilized to obtain diagnostic information by subtractively combining the digital information contained in two frames 94. For example, the digital information obtained from the optel 90 at each position of frame F4 can be subtracted from the corresponding digital information obtained from the optel 90 at each like position in frame F2. Workstation 6 can map these differences obtained for optels 90 at like positions to a gray scale and/or color scale to produce on display 12 a gray scale and/or color slope map image of the difference.

Figure 10:
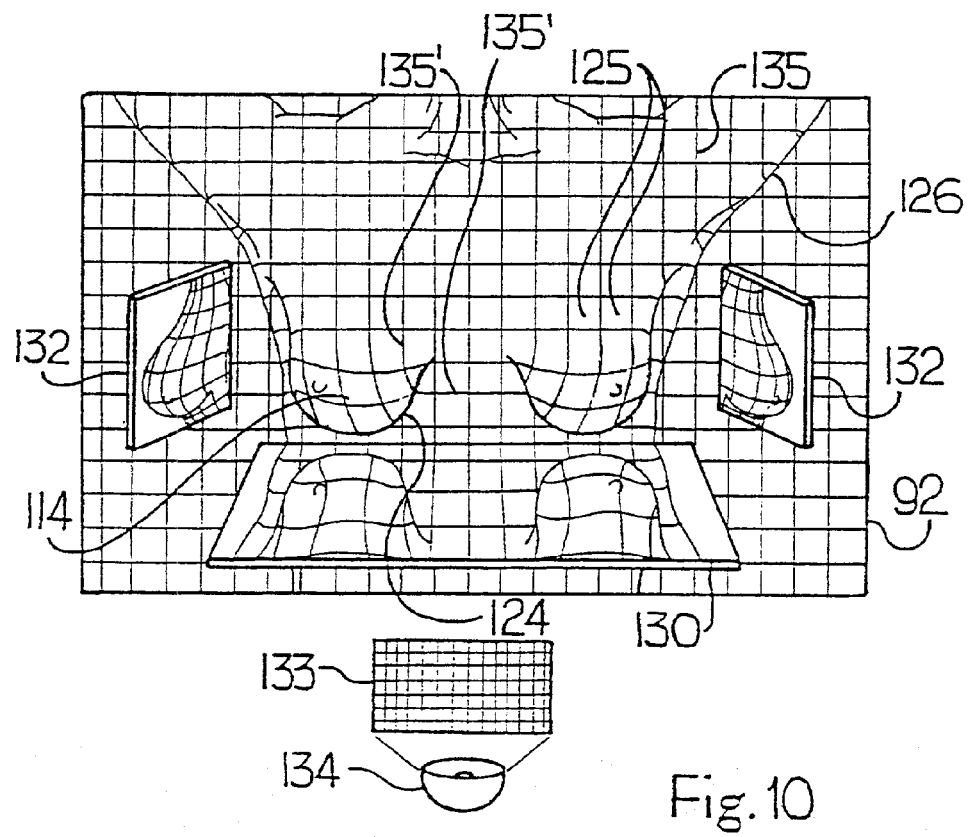
FIG. 10 is a schematic drawing of the patient shown in FIG. 7 including a sternum mirror below and lateral mirrors on opposite sides of the patient's breasts.

With reference to FIG. 10, and with reference back to FIGS. 2-7, a problem with IR imaging of breasts 114 is the difficulty associated with obtaining in certain patient P's IR images of the lower part 124 of breasts 114 regardless of the recline angle θ of patient P. Similarly, when IR imaging camera 4 is positioned in front of patient P in the manner shown in FIG. 6, IR images of a side 125 of each breast 114 adjacent arms 126 of patient P cannot be easily obtained without repositioning IR imaging camera 4. To enable IR imaging camera 4 to view the lower part 124 of each breast 114 as well as the side 125 of each breast 114 and the associated region of the axilla, a sternum mirror 130 is positioned below breasts 114 of patient P and lateral mirrors 132 are positioned on opposite sides 125 of breasts 114 of patient P. Sternum mirror 130 and lateral mirrors 132 are positioned so that lower part 124 of each breast 114 and side 125 of each breast 114 and the region of the axilla are within tFOV 92 and oriented to reflect IR radiation from lower part 124 of each breast 114 and side 125 of each breast 114 to IR imaging camera 4.

Utilizing image processing techniques, workstation 6 can construct gray scale and/or color slope map images of breasts 114 from IR radiation received directly from breasts 114 and the IR radiation reflected by mirrors 130 and 132. To enhance the ability of IR imaging camera 4 to detect a transition between mirrors 130, 132, patient P and the space therebetween, each mirror 130, 132 can include on one or more edges thereof viewable by IR imaging camera 4 a strip of material having an emissivity which is substantially different from the emissivity of a human being or other living animals or tissue. This particular application is of particular use in evaluating dermal sensitivity to exogenous materials, such as cosmetics, and provides a means of determining the rate of absorption through the skin of materials, such as a topically applied pharmaceuticals. This particular application provides an accurate quantitative and reproducible determination of dermal or skin sensitivity of human beings and other animals to chemical compounds and mixtures, such as cosmetics, thereby eliminating the need for certain controversial animal testing procedures, such as the "Draiz" test. The present invention also permits accurate quantitative and reproducible determinations of the rate of absorption or adsorption of topically applied medications and pharmaceuticals further eliminating the need for controversial animal testing procedures.

With reference back to FIG. 7, and with continuing reference to FIG. 10, to enable registration of successive frames 94 over time which may extend over the entire lifetime of patient P and to provide accurate superposition and consolidation of frames 94 from mirrors 130, 132 and to accommodate variations in perspective due to off-axis positioning of IR imaging camera 4, markers 158 can be placed at certain fixed anatomical landmarks such as the supracostal notch 160, the xiphisternal junction 162, the infraclavicular fossa 164, the anterior axillary line 166 and the acromion process 168. Markers 158 are made of a material with substantially different emissivity than that of patient P. In addition, certain useful anatomical landmark features can be identified from the information obtained by means of image processing techniques. With particular reference to the human breast, the existing bifurcations of the mammary vascular tree can be used as a means of image registration over time.

There are a number of means to enable front, side and/or bottom-up images, or three-dimensional images to be constructed from the IR radiation received directly from patient P and reflected from mirrors 130, 132. For example, a grid 133 can be positioned between a lamp 134, or other heat source, and the portion of patient P in tFOV 92 of IR imaging camera 4. At an appropriate time after acquiring frames 94, lamp 134 is energized thereby conveying thermal energy to the portion of patient P in tFOV 92 through grid 133. A portion of the thermal energy from lamp 134 is absorbed by grid 133 thereby causing the patient P to receive the thermal energy from lamp 134 in a grid-like pattern. Thermal energy received directly from lamp 134 forms on patient P an IR radiation pattern 135 that is grid-like when viewed directly on patient P and which follows the contour of patient P when viewed via mirrors 130, 132. Similarly, thermal energy received from lamp 134 via mirrors 130, 132 forms on patient P a reflected IR radiation pattern 135' that is grid-like when observed by IR imaging camera 4 through the mirrors 130, 132, but which follows the contour of the patient P when viewed directly from patient P. Utilizing image reconstruction techniques, workstation 6 can construct from IR radiation patterns 135 and 135' viewable directly and via mirrors 130, 132 front, side and/or bottom-up gray scale and/or color slope map images, or three-dimensional gray scale and/or color slope map images of breasts 114.

In another embodiment, patient P wears a nylon brassiere (not shown) with markers 158 positioned at select locations thereon that are viewable by IR imaging camera 4 directly or via mirrors 130, 132. Since nylon is transparent to IR radiation, workstation 6 can use the position of markers 158 on the brassiere to construct from the IR radiation patterns viewable directly and via mirrors 130, 132, front, side and/or bottom-up gray scale and/or color slope map images, or three-dimensional gray scale and/or color slope map images of breasts 114.

Figure 11:
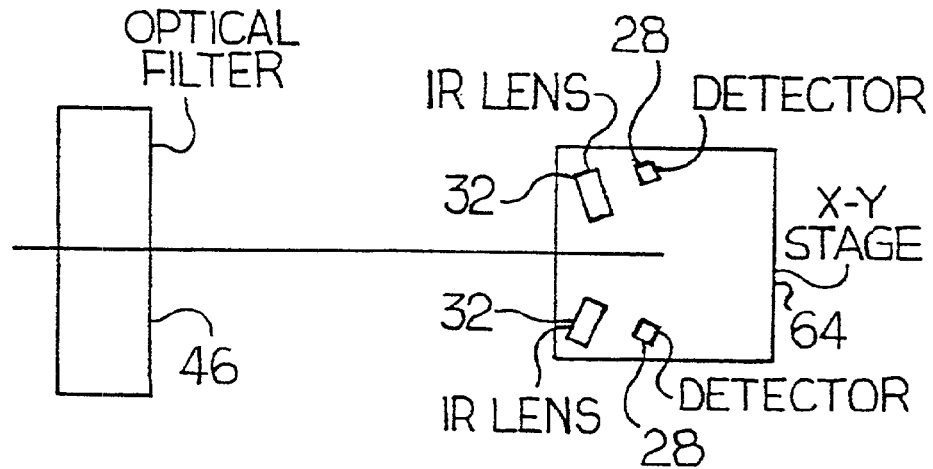
FIG. 11 is an isolated schematic drawing of a pair of detectors and a pair of infrared lens for acquiring stereoscopic images.

With reference to FIG. 11, and with reference back to FIG. 2. IR imaging camera 4 can be configured for stereoscopic imaging utilizing a pair of detectors 28 and a pair of IR lens 32 disposed on X-Y stage 64. The pair of detectors 28 and the pair of IR lens 32 are positioned on X-Y stage 64 to view and acquire IR radiation from a common optel 90 in tFOV 92 at the same time. X-Y stage 64 can be utilized to adjust the position of the pair of detectors 28 and the pair of IR lens 32 to view and acquire IR radiation from each optel 90 in tFOV 92. In this embodiment, preamplifier 76, image ADC 78 and image processing system 80 are configured to process the signal output by each detector 28 in response to receiving IR radiation from the same optel 90 at the same moment. The two images obtained for the optel 90 at each position in tFOV 92 can be combined by workstation 6 to produce a stereoscopic gray scale and/or color slope map image of the tissue of patient P subject to thermal stress.

Figure 12:
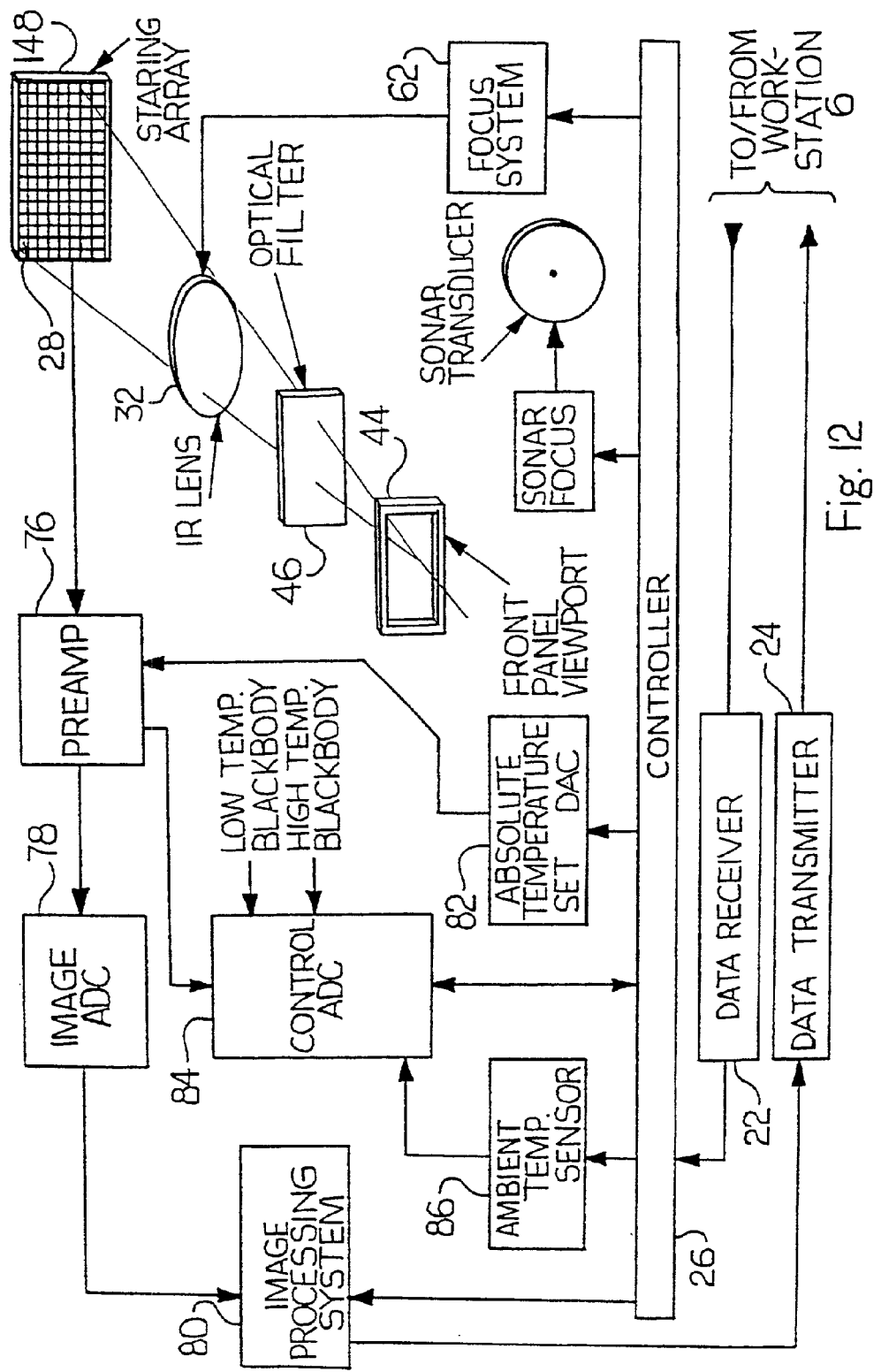
FIG. 12 is a block diagram drawing of the infrared imaging camera in FIG. 1 including a staring array of infrared detectors.

With reference to FIG. 12, and with continuing reference to FIG. 2, detector 28 can be replaced by an array 148 of detectors 28 positioned to receive IR radiation passing through front panel viewport 44, optical filter 46 and IR lens 32. In this embodiment, IR lens 32 has been "up-sized" to focus IR radiation received thereby on array 148 of detectors 28, commonly known as and referred to hereinafter as a "staring array" 148. In operation, controller 26 samples the output of each detector 28 of staring array 148 at substantially the same time, i.e., the frame sample interval, to form one frame 94 of the type shown in FIG. 3. Controller 26 obtains from staring array 148 at predetermined intervals, a plurality of frames 94. Using the method described above in connection with FIGS. 4 and 5, workstation 6 obtains for the optel 90 at like positions in each frame 94, a thermal response of the portion of patient P represented by the optel 90 over the imaging interval.

Figure 13:
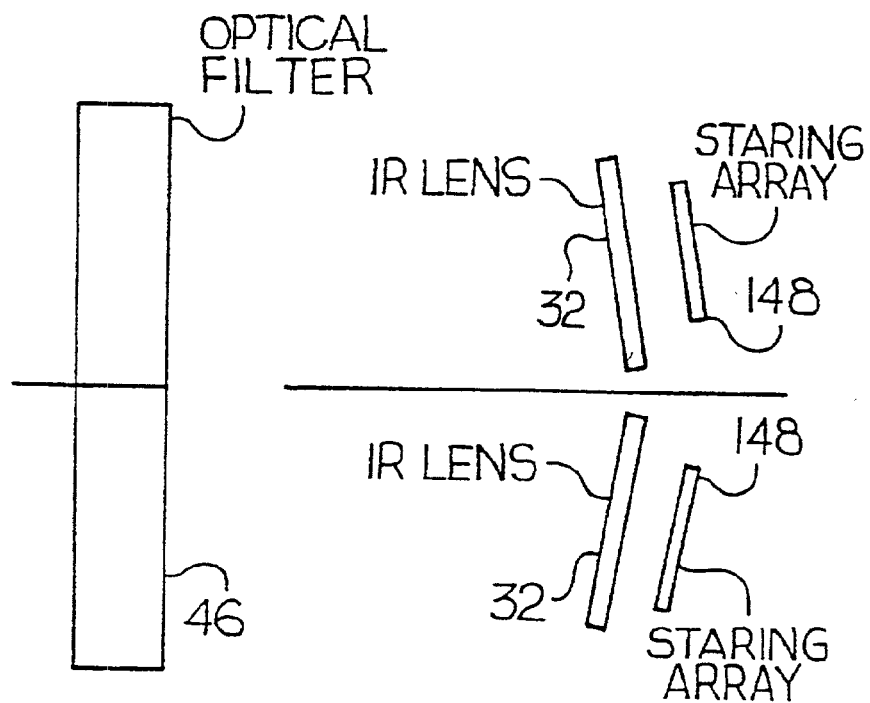
FIG. 13 is an isolated schematic drawing of a pair of infrared lens and a pair of staring arrays for acquiring stereoscopic images.

With reference to FIG. 13, and with reference back to FIGS. 11 and 12, a pair of staring arrays 148 and a pair of IR lens 32 can be utilized in the same manner of the pair of detectors 28 and the pair of IR lens 32 shown in FIG. 11 to produce stereoscopic images of patient P. In this embodiment, the pair of staring arrays 148 receives IR information from each optel 90 in tFOV 92, and preamplifier 76, image ADC 78 and image processing system 80 are configured to, process the image data received from each staring array 148. The two images obtained for the optel 90 at each position at tFOV 92 from the pair of staring arrays 148 can be combined by workstation 6 to produce a stereoscopic gray scale and/or color slope map image of the tissue of patient P subject to thermal stress.

In the embodiment shown in FIG. 11, each detector 28 can be configured to detect IR radiation at different wavelengths. For example, one detector 28 can be configured to detect IR radiation wavelengths between 1 and 2 microns and the other detector 28 can be configured to detect IR radiation wavelengths between 8 and 12 microns. In addition, each detector 28 configured to detect IR radiation at a specific wavelength can be paired with another like detector 28 in the manner shown in FIG. 11 to produce stereoscopic images of IR radiation at the different wavelengths. Preferably, each detector 28 is separated from another detector 28 by a distance greater than the size of the optel 90 viewable by each detector 28.

Preferably, the plurality of frames 94 of thermal images of patient P obtained over an imaging interval are stored in a patient data file in a nonvolatile memory, e.g., magnetic or optical data storage, of workstation 6 for subsequent local retrieval and analysis. The patient data file can also be transmitted to a distributed data system which stores plural patient data files for subsequent retrieval and analysis. The distributed data system preferably has a plurality of computers at different geographic locations that are interconnected in a manner known in the art, e.g., Internet. Each interconnected computer includes nonvolatile memory for receipt and storage of plural patient data files originating from local geographic locations, suitable operating system software and a suitable graphical user interface to facilitate user interaction with the computer. Preferably, each patient data file includes frames 94 of IR image data obtained over an imaging interval as well as other patient data, e.g., lifestyle habits, medical history and other risk factors, pertinent to an analysis of whether the patient is at risk for contracting breast cancer. Preferably, each patient data file is stored as a unique object in a relational database that is distributed among the computers of the distributed data system.

The operating system software of the distributed data system, preferably, supports an expert system that can analyze the plurality of patient data files, or a subset of the plurality of patient data files. Specifically, the expert system uses well-known analysis techniques, such as numerical statistical analysis, discriminate analysis or discriminate factor analysis to analyze a plurality of patient P data files or compare an individual patient P's data file with the plurality of patient P data files for statistical inconsistencies, e.g., those indicative of the angiogenesis associated with maturing neoplastic processes in the breast. Preferably, the expert system regularly compares the patient P data received with all the other patient P data in a plurality of patient P data files to identify statistically significant relationships and associations such as risk factors associated with the development of angiogenic activity or clinical manifestation of neoplastic disease.

The method and apparatus for IR imaging described herein can be used as a means of monitoring and objectively quantifying the effectiveness of both traditional pain treatment modalities, such as physical therapy and chiropractic manipulation and "non-traditional" pain treatment modalities, such as acupressure and acupuncture. Moreover, the method and apparatus can be used to determine appropriate points of application for certain pain treatment modalities, such as acupressure, acupuncture, massage therapy, trigger point injections, prolotherapy and application of focused electromagnetic energy, such as IR radiation.

In the evaluation of soft tissue injury, the IR imaging method and apparatus described herein can be used to obtain image series of the IR radiation from the skin over the whole body or lesser regions of interest over time by a variety of means including first surface mirrors of the creation of composite images by means of software.

Data obtained from detector 28 and/or staring array 148 can be utilized to determine axes of symmetry of contralateral muscles groups, dermatomes and thermatomes. Statistical methods can be utilized to determine whether there are statistically significant differences in the IR radiation from comparable contralateral areas. If so, the analysis is continued to determine whether there are statistically significant differences between symmetrical areas within each contralateral group.

For example, a statistically significant difference in the IR energy emitted from the surface of the skin associated with the right arm when compared to the left arm might merely indicate that patient P is right-handed. However, further statistical analysis of each arm independently, based on considerations of internal symmetries of the biceps muscle group and the triceps muscle group, for example, followed by statistical analysis and comparison of the internal symmetry relationships within each comparable muscle group eliminates the effect of "handedness." This method of analysis is of great importance in dealing with complaints of pain associated with broad flat muscle areas, such as the trapezius muscles, the latissimus dorsi group and other areas of the back.

Accurate location of multiple axes of symmetry of contralateral muscle groups, dermatomes and thermatomes permits accurate registration of subsequent image time series and quantitative evaluation of the effectiveness of treatment. Mapping the IR radiation data to surficial anatomical landmarks and displaying the information to the health care practitioner in real-time can improve the efficiency and effectiveness of treatment.

The invention has been described with reference to the preferred embodiments. Obvious modifications and alterations will occur to others upon reading and understanding the preceding description. It is intended that the invention be construed as including all such modifications and alterations insofar as they come within the scope of the appended claims or the equivalents thereof.

We claim:

1. A method of producing images of infrared (IR) radiation of a patient, the method comprising the steps of:
   (a) providing an IR imaging camera configured to receive IR radiation from an array of optical elements (optels) in a field-of-view viewable by the IR imaging camera;
   (b) acquiring a plurality of frames of IR radiation from a patient positioned in the field-of-view, with each frame acquired during a corresponding frame sample interval, with each frame corresponding to the IR radiation acquired from the array of optels during its frame sample interval;
   (c) determining plural rates of change as a function of the IR radiation acquired from the array, with each rate of change corresponding to a change of the IR radiation received from the same optel in at least two frames;
   (d) mapping each rate of change to a color or a shade of gray; and
   (e) mapping the color or the shade of gray of each rate of change to a position in an image corresponding to the position of the corresponding optel in the field-of-view.

2. The method as set forth in claim 1, wherein:
   the plurality of frames are acquired over an imaging interval; and
   the acquisition occurrence of each frame is fixed or variable.

3. The method as set forth in claim 1, further including the step of adjusting for the absolute temperature of the IR radiation acquired from each optel.

4. The method as set forth in claim 1, wherein in step (c) determining each rate of change includes determining a first derivative or a second derivative.

5. The method as set forth in claim 1, wherein step (b) includes the step of sequentially acquiring IR radiation from each optel in the field-of-view during the frame sample interval.

6. The method as set forth in claim 1, wherein step (b) includes the step of acquiring IR radiation from all of the optels in the field-of-view at substantially the same time.

7. The method as set forth in claim 2, wherein step (b) includes the steps of:
   exposing the patient to ambient temperature air;
   initiating the acquisition of frames;
   exposing the patient to a flow of conditioned air at a temperature different than the ambient temperature; and
   terminating the acquisition of frames after the imaging interval.

8. The method as set forth in claim 1, further including the step of positioning at least one marker on the patient and in the field-of-view, the at least one marker having an emissivity different than the emissivity of the patient.

9. The method as set forth in claim 8, wherein the at least one marker is positioned on a fixed anatomical location of the patient.

10. The method as set forth in claim 1, further including the steps of:
    positioning at least one mirror in the field-of-view adjacent the patient; and
    orienting the at least one mirror to reflect IR radiation from a part of the patient that is the field-of-view but is concealed from the IR imaging camera by another part of the patient.

11. The method as set forth in claim 10, further including the steps of:
    positioning a grid between the IR imaging camera and the patient;

conveying thermal energy to the patient through the grid; and acquiring a frame of IR radiation directly from the patient and from the at least one mirror.

12. The method as set forth in claim 10, further including the step of constructing a three-dimensional image of the patient from the IR radiation acquired directly from the patient and acquired from the at least one mirror.

13. An infrared imaging apparatus comprising:

means for detecting IR radiation from each optical element (optel) of an array of optels forming a field-of-view of the imaging apparatus;

a controller for controlling the means for detecting to selectively acquire a plurality of frames of IR radiation from the array at a like plurality of sample intervals, with each frame corresponding to the IR radiation acquired from all of the optels of the array during one sample interval; and a workstation for determining plural rates of change as a function of IR radiation received by the means for detecting from the array, with each rate of change corresponding to a change of IR radiation acquired from the same optel in at least two frames, wherein the workstation:

maps each rate of change to a color or a shade of gray; and maps the color or the shade of gray of each rate of change to a position in an image corresponding to the position of the corresponding optel in the field-of-view.

14. The infrared imaging apparatus as set forth in claim 13, further including means for converting IR radiation acquired from each optel into corresponding data, wherein the workstation determines the rate of change for each optel from the data corresponding to the IR radiation acquired from the optel in at least two frames.

15. The infrared imaging apparatus as set forth in claim 13, further including at least one mirror positioned adjacent a patient received in the field-of-view, wherein:

the at least one mirror is received in the field-of-view; and the at least one mirror is oriented to reflect IR radiation from a part of the patient that is within the field-of-view but is concealed from the means for detecting by another part of the patient.

16. An infrared imaging apparatus comprising:

means for detecting IR radiation from each optical element (optel) of an array of optels forming a field-of-view of the imaging apparatus;

means for controlling the means for detecting to selectively acquire a plurality of frames of IR radiation from the array at a like plurality of sample intervals, with each frame corresponding to the IR radiation acquired from all of the optels of the array during one sample interval; and means for determining plural rates of change as a function of IR radiation received by the means for detecting from the array, with each rate of change corresponding to a change of IR radiation acquired from the same optel in at least two frames, wherein the means for determining:

maps each rate of change to a color or a shade of gray; and maps the color or the shade of gray of each rate of change to a position in an image corresponding to the position of the corresponding optel in the field-of-view.

17. The infrared imaging apparatus as set forth in claim 16, further including means for converting IR radiation acquired from each optel into corresponding data, wherein the means for determining further determines the rate of change for each optel from the data corresponding to the JR radiation acquired from the optel in at least two frames.

18. The infrared imaging apparatus as set forth in claim 16, wherein the means for controlling further controls the means for detecting to acquire the plurality of frames over an imaging interval, wherein the acquisition occurrence of each frame is fixed or variable.

19. The infrared imaging apparatus as set forth in claim 16, wherein the means for controlling further controls the means for detecting to acquire the plurality of frames logarithmically over an imaging interval, wherein the acquisition occurrence increases late in the imaging interval.

20. The infrared imaging apparatus as set forth in claim 16, wherein the means for determining further determines the rate of change corresponding to a change of IR radiation acquired from the same optel in at least two frames that are separated in time by at least one frame.

21. The infrared imaging apparatus as set forth in claim 16, wherein the means for controlling further controls the means for detecting to acquire frames in synchronization with heartbeat cycles of a patient received in the field-of-view and the at least two frames are acquired during like portions of two different heartbeat cycles.

* * * * *

UNITED STATES PATENT AND TRADEMARK OFFICE
CERTIFICATE OF CORRECTION

PATENT NO.         : 8,233,968 B1                              Page 1 of 1
APPLICATION NO.    : 10/019904
DATED              : July 31, 2012
INVENTOR(S)        : Victor John Yannacone, Jr. et al.

It is certified that error appears in the above-identified patent and that said Letters Patent is hereby corrected as shown below:

Column 16, Line 61, Claim 10, after "is" insert -- within --

Column 18, Line 22, Claim 17, delete "JR" and insert -- IR --

Signed and Sealed this
Thirteenth Day of November, 2012

David J. Kappos
*Director of the United States Patent and Trademark Office*